(12) United States Patent
Thiel et al.

(10) Patent No.: US 7,279,075 B2
(45) Date of Patent: Oct. 9, 2007

(54) THERMAL SEPARATING PROCESS BETWEEN AT LEAST ONE GASEOUS AND AT LEAST ONE LIQUID STREAM, OF WHICH AT LEAST ONE COMPRISES (METH)ACRYLIC MONOMERS

(75) Inventors: Joachim Thiel, Neustadt (DE); Hugues Vandenmersch, Wachenheim (DE); Juergen Schroeder, Ludwigshafen (DE); Albrecht Dams, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 450 days.

(21) Appl. No.: 10/647,241

(22) Filed: Aug. 26, 2003

(65) Prior Publication Data

US 2004/0138501 A1    Jul. 15, 2004

(30) Foreign Application Priority Data

Jan. 10, 2003   (DE) ................... 103 00 816

(51) Int. Cl.
*B01D 3/42* (2006.01)
*C07C 51/42* (2006.01)

(52) U.S. Cl. .............. 203/1; 203/8; 203/100; 203/40; 261/114.5; 562/600

(58) Field of Classification Search ........... 203/1, 203/8, 40, 100, DIG. 21; 261/2, 28, 114.1–114.5; 95/210; 562/600
See application file for complete search history.

(56) References Cited

U.S. PATENT DOCUMENTS

| 3,717,553 A | | 2/1973 | Otsuki et al. | |
| 4,068,053 A | * | 1/1978 | Miserlis et al. | 526/68 |
| 4,578,153 A | * | 3/1986 | Newton | 203/99 |
| 4,820,385 A | * | 4/1989 | Cova et al. | 203/2 |
| 6,294,056 B1 | * | 9/2001 | Matsumoto et al. | 203/90 |
| 6,345,811 B1 | * | 2/2002 | Yu et al. | 261/97 |
| 6,413,379 B1 | | 7/2002 | Machhammer et al. | |
| 6,787,001 B2 | * | 9/2004 | Sakamoto et al. | 203/2 |
| 2002/0043454 A1 | | 4/2002 | Machhammer et al. | |

FOREIGN PATENT DOCUMENTS

| DE | 1 029 573 | 5/1958 |
| DE | 2 027 655 | 1/1971 |
| DE | 196 06 877 | 8/1997 |
| DE | 199 24 532 | 11/2000 |
| DE | 101 15 277 | 6/2002 |
| DE | 101 59 825 | 6/2003 |
| DE | 102 18 419 | 6/2003 |
| DE | 102 24 341 | 7/2003 |
| EP | 0 937 488 | 8/1999 |
| EP | 0 982 287 | 3/2000 |
| EP | 0 982 289 | 3/2000 |
| EP | 1 029 573 | 8/2000 |
| EP | 1 044 957 | 10/2000 |
| EP | 1 125 912 | 8/2001 |
| WO | WO 00/53561 | 9/2000 |

* cited by examiner

*Primary Examiner*—Virginia Manoharan
(74) *Attorney, Agent, or Firm*—Oblon, Spivak, McClelland, Maier & Neustadt, P.C.

(57) ABSTRACT

In a thermal separating process between at least one gaseous and at least one liquid stream, of which at least one comprises (meth)acrylic monomers, in a separating column containing sieve trays as separating internals, at least some of the sieve trays are operated above an entrainment fraction of 10% by weight.

11 Claims, No Drawings

THERMAL SEPARATING PROCESS BETWEEN AT LEAST ONE GASEOUS AND AT LEAST ONE LIQUID STREAM, OF WHICH AT LEAST ONE COMPRISES (METH)ACRYLIC MONOMERS

The present invention relates to a thermal separating process between at least one gaseous and at least one liquid stream, of which at least one comprises (meth)acrylic monomers, in a separating column containing separating internals, at least some of the separating internals being a sequence of sieve trays.

In this document, the notation (meth)acrylic monomers is an abbreviation of "acrylic monomers and/or methacrylic monomers".

In this document, the term acrylic monomers is an abbreviation of "acrolein, acrylic acid and/or esters of acrylic acid".

In this document, the term methacrylic monomers is an abbreviation of "methacrolein, methacrylic acid and/or esters of methacrylic acid".

In particular, the (meth)acrylic monomers addressed in this document are intended to include the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparing polymers which find use, for example, as adhesive.

(Meth)acrolein and (meth)acrylic acid are prepared on the industrial scale predominantly by catalytic gas phase oxidation of suitable C3/C4 precursor compounds (or of precursor compounds thereof), in particular of propene and propane in the case of acrolein and acrylic acid, or isobutene and isobutane in the case of methacrylic acid and of methacrolein. However, also suitable as starting materials in addition to propene, propane, isobutene and isobutane are other compounds containing 3 or 4 carbon atoms, such as isobutanol, n-propanol or precursor compounds thereof, for example the methylether of isobutanol. (Meth)acrylic acid can also be obtained from (meth)acrolein.

This normally results in a product gas mixture from which the (meth)acrylic acid and/or the (meth)acrolein have to be removed.

Esters of (meth)acrylic acid are obtainable, for example, by direct reaction of (meth)acrylic acid and/or (meth)acrolein with the appropriate alcohols. However, product mixtures are initially obtained in this case also, from which the (meth)acrylic esters have to be removed.

For the aforementioned removals, separating processes are frequently employed which are carried out in separating columns containing separating internals. In these separating columns, gaseous (rising) and liquid (falling) streams are frequently conducted in countercurrent, and, as a consequence of the inequilibrium existing between the streams, heat and mass transfer takes place which ultimately results in the separation desired in the separating column. In this document, such separating processes are to be referred to as thermal separating processes.

Examples of and therefore elements of the term "thermal separating processes" used in this document are fractional condensation (cf. DE-A 19924532) and/or rectification (rising vapor phase is conducted in countercurrent to falling liquid phase; the, separating action is based on the vapor composition at equilibrium being different to the liquid composition), absorption (at least one rising gas is conducted in countercurrent to at least one falling liquid; the separating action is based on the different solubility of the gas constituents in the liquid), stripping (like absorption; however, the liquid phase is laden with a component which is taken up by the stripping gas) and desorption (the reverse process to absorption; the gas dissolved in the liquid phase is removed by partial pressure reduction).

For example, the removal of (meth)acrylic acid and/or (meth)acrolein from the product gas mixture of the catalytic gas phase oxidation can be carried out in such a way that the (meth)acrylic acid and/or the (meth)acrolein are initially removed in a basic manner by absorption in a solvent (for example water or an organic solvent) or by fractional condensation of the product gas mixture, and the resulting condensate or absorbate is subsequently rectificatively separated (generally in a plurality of stages) to obtain more or less pure (meth)acrylic acid and/or (meth)acrolein (cf., for example, EP-A 717019, EP-A 1125912, EP-A 982289, EP-A 982287, DE-A 19606877, DE-A 1011527, DE-A 10224341 and DE-A 10218419).

The fractional condensation addressed above differs from conventional rectification essentially in that the mixture to be separated is fed to the separating column in gaseous form (i.e. completely converted to vapor form).

The gaseous or liquid mixtures which comprise (meth)acrylic monomers and have already been addressed above may contain the (meth)acrylic monomers either in more or less pure form or in dilution (e.g. with solvent or with diluent gases). The solvent may be either aqueous or an organic solvent, and the specific type of the organic solvent is substantially insignificant. The diluent gas may be, for example, nitrogen, carbon oxide (CO, $CO_2$), oxygen, hydrocarbon or a mixture of these gases.

In other words, for example on the route to obtaining (meth)acrylic monomers, thermal separating processes are applied in a highly differing manner to gaseous and/or liquid mixtures whose content of (meth)acrylic monomers is $\geq 2\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

The (meth)acrylic monomers can accumulate either at the top or at the bottom of the separating column. However, it will be appreciated that fractions comprising accumulated (meth)acrylic monomers can also be withdrawn in the upper, lower or middle region of the separating column.

In the thermal separating processes, the separating internals contained in the separating columns fulfil the purpose of increasing the surface area for the heat and mass transfer effecting the separation in the separating column.

Examples of useful internals include structured packings, random packings and/or mass transfer trays.

Particularly frequently, the separating columns used are those which contain a sequence of mass transfer trays at least as a portion of the separating internals.

Mass transfer trays fulfil the purpose of providing locations with continuous liquid phases in the separating column, in the form of liquid layers. The surface of the vapor or gas stream rising in the liquid layer and being distributed in the continuous liquid phase is then the decisive exchange surface.

A classic among the mass transfer trays is the sieve tray. In this document, this refers to plates which have simple holes and/or slots as passages for the rising gas or vapor phase (the terms "gaseous" and "vaporous" are used synonymously in this document).

The sieve trays are differentiated into two groups, namely into those having forced liquid flow and those without forced liquid flow.

The forced liquid flow is achieved by the sieve trays, in addition to the passages for the rising gas or vapor phase, having at least one downcomer, (outlet) through which the liquid flows, irrespective of the flow path of the vapor, from the higher tray to the next lowest tray (inlet). The liquid flows in crossflow over the tray from at least one inlet to at least one outlet, and the outlet and inlet pipes guarantee the liquid seal and the desired liquid level on the tray. Frequently (especially in the case of small column diameters), the sieve trays are configured with single flow and forced liquid flow. In other words, inlet and outlet are arranged on opposite sides of the tray. However, they may also be configured with double flow (or even more than double flow). In this case, the feed may, for example, be arranged in the middle and one outlet each on opposite sides of the mass transfer tray. Such sieve trays are to be referred to hereinbelow as forced sieve trays. In the case of these trays, trickle-through of the liquid, which reduces the separating action, is not prevented, as in the case of bubble-cap trays, by chimneys into which the passages continue, but rather a minimum vapor loading is required for this purpose. The vapor rises through the passages and bubbles through the liquid layer held by the outlet pipe.

The dual-flow trays, or trickle sieve trays, differ from the forced sieve trays in that they contain no outlet segment. In the case of the dual-flow trays, the absence of outlet segments (downcomers) results in the rising gas and the liquid falling in the separating column passing through the same passages of the tray. As in the case of forced sieve trays, a minimum vapor loading is required in the case of dual-flow trays, in order to achieve an appropriate separating action. When the vapor loading is significantly lower, rising gas and falling reflux move past each other substantially without exchange and the tray is at risk of running dry. In other words, in the case of dual-flow trays also, a lower limiting flow rate has to be present, so that a certain liquid layer is maintained on the tray, in order to enable the tray to work. In the normal working range, in the case of dual-flow trays, the liquid trickles through the passages from tray to tray, and the continuous gas phase is interspersed by a divided liquid phase between the trays. The drops landing on the dual-flow trays are partially atomized.

While one advantage of sieve trays over bubble-cap trays is based on their simpler design, one of the disadvantages is that in their case, the constant upward flow direction of the vapor increases the tendency toward entrainment of small liquid droplets. As a consequence of the entrainment of liquid by the rising vapor from a lower sieve tray to the next highest sieve tray, the countercurrent flow of gas and liquid phase in the separating column is impaired. This results in backmixing of the liquid over the sieve trays, which reduces the condensation gradient driving the mass transfer and thus the mass transfer between the phases and therefore ultimately the separating action.

The proportion by weight of the total amount of liquid which is fed to a sieve tray in an operating separating column and is entrained by the rising gas to the next highest sieve tray is to be referred to hereinbelow as the entrainment fraction (in % by weight) of this sieve tray.

In principle, the entrainment fraction of a sieve tray in an operating separating column (carrying out a thermal separating process) can be determined experimentally. For example, in a rectification in a separating column whose separating internals are exclusively dual-flow trays in equidistant separation d, a chimney tray (for example one according to DE-A 10159825) can be mounted at a separation d above the uppermost dual-flow tray. The vapor phase rising through the chimney tray is conducted out of the column and condensed in a condenser. A portion of the condensate is removed as pure product and the remaining portion recycled into the separating column as reflux liquid between the chimney tray and the uppermost sieve tray. The reflux liquid forms the first portion of the total amount of the amount of liquid fed to the uppermost sieve tray. In the event of passage of the vapor phase through the chimneys of the chimney tray, entrained liquid droplets disposed in the vapor phase condense out on the chimney tray (collecting tray). The liquid phase which forms as a result on the chimney tray is continuously withdrawn from it, quantified and fed as the second portion of the reflux liquid. The entrainment fraction of the uppermost sieve tray can be determined from the total amount and second portion. This shows that the entrainment fraction is substantially independent of the precise point at which the reflux liquid is recycled into the separating column between chimney tray and uppermost dual-flow tray.

For other tray locations, the entrainment fraction can be determined experimentally in a similar manner. This shows that the entrainment fraction within the separating column changes only slightly from top to bottom in the case of a thermal separating process in a column containing sieve trays only and having identical, equidistantly arranged sieve trays in not too large a total number.

Since the pressure is increased in the lower section of a separating column, the mass density increases from top to bottom in a thermal separating process in a separating column, and for this reason, a certain mass flow is achieved in the lower column section even at a comparatively relatively low gas flow rate, which ultimately results in a relatively low entrainment fraction.

It has also become possible to calculate the entrainment fractions of sieve trays from hydrodynamic parameters and also the tray design (for example hole diameter, hole separation, orifice ratio, tray separation etc.).

Another area of problems when carrying out thermal separating processes between at least one gaseous and at least one liquid stream, of which at least one comprises (meth)acrylic monomers, in a separating column containing sieve trays is that (meth)acrylic monomers are very reactive with respect to free-radical polymerization and tend toward undesired polymerization. Such undesired polymerization is critical especially on the underside of sieve trays, since these are substantially dry in the customary operation of a thermal separating process in a separating column containing sieve trays. Polymer forming on the underside in normal operation can therefore grow substantially undisturbed and the sieve trays of a separating column ultimately block after only a short operating time and make the further operation of a separating column impossible.

An improvement can be achieved by following the teaching of DE-A 2027655 to use sieve trays having specially shaped holes whose hole shape ensures that liquid reflux continuously moistens the tray underside after passing through the holes. Polymerization nuclei forming on the tray underside are thus continuously washed away and transported into the column bottom, which reduces polymer growth on the sieve tray underside. A further improvement is achieved when the separating column is operated with polymerization inhibition. In other words, as is customary in thermal separating processes involving (meth)acrylic monomers, polymerization inhibitors (e.g. phenolic compounds, amino compounds, nitro compounds, phosphorus compounds, sulfur compounds, N-oxyl compounds and/or heavy metal salts) are added to the liquid phase falling in the separating column. According to DE-A 2027655, moistening of the tray underside leads in this case automatically to polymerization inhibition of the sieve tray underside.

However, a disadvantage of the procedure of DE-A 2027655 is that the special shape of the holes negates the substantial advantage of sieve trays, namely their ease of production.

EP-A 937488 and EP-A 1044957 describe processes for rectifying mixtures comprising (meth)acrylic monomers, in which the interior surface area of the rectification column, including the tray underside, is sprayed with polymerization-inhibited reflux via nozzles.

A disadvantage of this procedure is that it requires additional apparatus.

For polymerization reduction in processes for rectifying mixtures comprising (meth)acrylic monomers, EP-A 1029573 recommends the use of dual-flow trays whose hole diameter, hole separations, tray thicknesses, orifice ratios, hole shape, tray separation and liquid loading are within comparatively narrowly defined ranges. However, these measures for reducing undesired free-radical polymerization of (meth)acrylic monomers are also not fully satisfactory.

It is an object of the present invention, under the aspect of reducing undesired polymer formation, to provide an improved thermal separating process between at least one gaseous and at least one liquid stream, of which at least one comprises (meth)acrylic monomers, in a separating column containing separating internals, at least some of the separating internals being a sequence of sieve trays.

We have found that this object is achieved by a thermal separating process between at least one gaseous and at least one liquid stream, of which at least one comprises (meth)acrylic monomers, in a separating column containing separating internals, at least some of the separating internals being a sequence of sieve trays, which comprises selecting the streams in such a way that at least some of the sieve trays are operated above an entrainment fraction of 10% by weight.

What is surprising about the invention is that, in contradiction to the current teaching (for example Johann Stichlmair in Grundlagen der Dimensionierung des Gas-/Flüssigkeit-Kontaktapparates, Bodenkolonne, Verlag Chemie, Weinheim, 1978, p.131), the separating action of sieve trays is reduced hardly perceptibly even in the case of entrainment fractions of up to 30% by weight.

However, an increased entrainment fraction automatically leads to increased moistening of the tray undersides in a sieve tray sequence disposed within a separating column and thus reduces the undesired polymer formation in a similar, but simpler manner than described in DE-A 2027655. This is especially true when the liquid phase falling in the separating column in the thermal separating process according to the invention contains added polymerization inhibitors in a manner known per se. Such a polymerization inhibitor may also be a molecular oxygen-containing gas conducted through the separating column with the rising vapor or jetted in at various points in the separating column. In the simplest manner, such a molecular oxygen-containing gas may be air (cf., for example, DE-A 10248606, DE-A 10238142 and DE-A 10217121).

In other words, the entrainment fraction of at least some of the sieve trays when carrying out the process according to the invention without significantly reducing the separating action may be from >10 to 30% by weight, or from 11 to 30% by weight, or from 12 to 30% by weight, or from 13 to 30% by weight, or from 14 to 30% by weight, or from 15 to 30% by weight. The upper limit of the ranges mentioned, instead of 30% by weight, may also be 28% by weight, or 25% by weight, or 20% by weight.

According to the invention, preference is given to carrying out the thermal separating process according to the invention in such a way that the entrainment fraction of at least half and more preferably at least 75% or all sieve trays is within the aforementioned ranges. In particular, those sieve trays at which the content of (meth)acrylic monomers is particularly high are within the aforementioned ranges.

This is especially true when the separating internals of the separating column are exclusively sieve trays (forced sieve trays and/or dual-flow trays). It is especially true when the sequence of the sieve trays in the process according to the invention is equidistant.

When practicing the process according to the invention, if a reduction is observed in the separating action of the sequence of sieve trays contained in the separating column compared with the normal operation of the sieve trays according to the teaching of the prior art, this can be compensated by increasing the number of sieve trays at constant separation (i.e. the column height).

From an application point of view, the sieve tray separation within the sieve tray sequence should be within the range from 300 to 900 mm. According to the invention, preference is given to the sieve tray separation within the sieve tray sequence in the process according to the invention being from 300 to 500 nm. In general, the sieve tray separation should not be less than 250 mm.

By means of the measure of increasing the number of sieve trays, it is possible in the process according to the invention to increase the entrainment fraction of the sieve trays to values of up to 70% by weight without significantly impairing the separating action. In other words, the upper limit of the entrainment fraction of at least some of the sieve trays when carrying out the process according to the invention for the ranges already mentioned, instead of 30% by weight, may also be 35% by weight, or 40% by weight, or 50% by weight, or 60% by weight, or 70% by weight. It will be appreciated that the entrainment fractions of all sieve trays in the process according to the invention may also be within this extended entrainment fraction.

Useful (meth)acrylic monomers for the process according to the invention may be any of those which have been mentioned at the outset of this document. It may be a fractional condensation, or a rectification, or an absorption, or a stripping, or a desorption.

In particular, the process according to the invention can be applied to all thermal processes for removing (meth)acrylic monomers from the mixtures mentioned at the outset of this document.

The content in the gaseous and/or liquid mixtures of (meth)acrylic monomers may be $\geq 2\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

The sieve trays themselves in the process according to the invention may be designed as described in DE-A 2027655, DE-A 10156988, DE-A 10230219, EP-A 1029573 or in Grundlagen der Dimensionierung von Kolonnenböden, Technische Fortschrittsberichte, Volume 61, K. Hoppe, M.

Mittelstrass, Verlag Theodor Steinkopff, Dresden 1967. The passages may be circular, elliptical or polygonal. They may also have any other shape (for example slot-shaped). According to the invention, they are preferably circular and arranged in strict triangular pitch. For example, the hole diameter of the sieve trays (in particular in the case of dual-flow trays) may be from 5 to 50 mm, preferably from 10 to 25 mm. The separation of two immediately adjacent hole centers is advantageously from 1.5 to 3 times, preferably from 2 to 2.8 times, the hole diameter, which is preferably uniformly dimensioned over the individual sieve trays.

The orifice ratio (ratio of the total surface area of all passages of the sieve tray to the total surface area of the sieve tray multiplied by 100 and in %) in sieve trays to be used in accordance with the invention is advantageously from 8 to 30% and frequently from 12 to 20%. The tray thickness is advantageously from 1 to 8 mm.

Processes according to the invention are, for example, rectifications or fractional condensations which are carried out in separating columns whose separating internals are exclusively trays of whose number at least two, preferably more than two (preferably $\geq 10\%$, or $\geq 20\%$, or $\geq 30\%$, or $\geq 40\%$, or $\geq 50\%$, or $\geq 60\%$, or $\geq 75\%$) and more preferably all sieve trays, are particularly advantageously dual-flow trays having circular passages.

The remaining trays may, for example, be hydraulically sealed crossflow trays (for example Thormann trays or bubble-cap trays) and/or valve trays.

The gas loading factor F of the sequence of sieve trays to be used in accordance with the invention is in practice in many cases in the range from 1 to 3 $Pa^{0.5}$, frequently in the range from 1.5 to 2.5 $Pa^{0.5}$. The liquid flow rate is at the same time often in the range from 1 to 50 m/h or in the range from 2 to 10 m/h.

As already mentioned, the process according to the invention, especially in the case of rectification or absorption, is normally operated with polymerization inhibition. To this end, the polymerization inhibitors are generally added at the top of the separating column to the liquid phase falling in the separating column (for example the reflux liquid or the absorbent). Typical polymerization inhibitors which can be used in accordance with the invention include phenothiazine, hydroquinone and the monomethyl ether of hydroquinone. As a further stabilization measure, as likewise already described, a molecular oxygen-containing gas, e.g. air, can additionally be conducted through the separating column. In advantageous cases, polymerization can even be inhibited using exclusively air.

Advantageously, in the case of dual-flow trays used in accordance with the invention, transverse mixing and large-surface-area wave movements on the dual-flow trays are prevented by perpendicular, flat internals, known as baffles. From an application point of view, the baffles in their industrial scale use are advantageously from 50 to 300 mm, preferably from 150 to 200 mm high, and from 500 to 6000 mm, preferably from 1000 to 3000 mm long (their length may be the same as the tray diameter or part of the tray diameter). Preferably, their lower edge does not sit directly on the upper side of the dual-flow tray, but is rather supported by means of small feet or separators on the dual-flow tray in such a way that the separation of their lower edge to the upper side of the dual-flow tray is from 10 to 60 mm, preferably from 30 to 50 mm. The number of separators per baffle is from 1 to 10. From an application point of view, the separation of the baffles from each other is advantageously from 100 to 1000 mm, frequently from 150 to 500 mm. The surface segments between two baffles are normally $\geq 0.2$ m$^2$, but usually $\leq 5$ m$^2$, which limits the number of baffles per dual-flow tray.

The above measures are suitable in particular for a preferred variant of the dual-flow trays of the example and comparative example in the documents DE-A 10243625 and DE-A 10247240.

An increase in the entrainment fraction in a separating column to be operated in accordance with the invention is possible in a simple manner, for example, by covering some of the passages of the sieve trays at constant loading.

It will be appreciated that the process according to the invention can also be applied in combination with individual or all measures mentioned in DE-A 2027655, EP-A 937488, EP-A 1044957 and EP-A 1029573 which reduce undesired polymerization.

Quite generally, the process according to the invention can be carried out under atmospheric pressure, increased pressure or under reduced pressure.

In particular, the process according to the invention is suitable for the fractional condensations described in DE-A 19924532, DE-A 10243625 and DE-A 10247240 of product gas mixtures which comprise acrylic acid and are from heterogeneously catalyzed gas phase partial oxidations of $C_3$ precursors of acrylic acid with molecular oxygen in separating columns which from bottom to top contain initially dual-flow trays followed by hydraulically sealed crossflow mass transfer trays.

The process according to the invention is characterized by a reduced tendency to undesired polymer formation at simultaneously increased throughput (kg of product per hour).

It will be appreciated that even in the process according to the invention, excessively high gas loading factors or liquid flow rates no longer allow the liquid to sufficiently flow downward from the sieve trays, and the dual-flow trays can flood. Beyond the flooding limit, no viable column operation is possible.

In general, the sieve trays used, in particular the dual-flow trays used, in the process according to the invention are joined flush to the column walls. However, there are also embodiments in which there is an intermediate space between column wall and tray which is only partly interrupted by bridges. In addition to the actual passages, dual-flow trays used in the process according to the invention, if need be, have further orifices which enable, for example, securing of the tray to support rings or the like (cf., for example, DE-A 10159823).

The process according to the invention is also suitable in particular for the rectification described by way of example in DE-A 10230219 and also for the absorption described in EP-A 925272 in stage (b).

EXAMPLES AND COMPARATIVE EXAMPLE a) Comparative Example

A separating column according to Example 1 of DE-A 10247240 (height 54.3 m; internal diameter in the region of the Thormann trays 6.5 m, otherwise 6.0 m) contained from bottom to top initially 15 dual-flow trays (hole diameter a uniform 14 mm, number of holes a uniform 33678, orifice ratio a uniform 18%, equidistant tray separation 380 mm, strict triangular pitch of the centers of the passage circles, punched burr of the passage holes pointing downward, separation of two immediately adjacent passage hole centers 30 mm) which are completed by a first collecting tray; 2.9 m above this collecting tray, 21 further dual-flow trays of the type described, except number of holes a uniform 32020 and orifice ratio a uniform 17.4%; 1.50 m above the last dual-flow tray commencement of an equidistant (tray separation=500 mm) arrangement of 28 conventional single-flow Thormann trays (having successive channels in the crossflow direction each having the opposite flow direction to each other, orifice ratio 14%, ratio of chimney surface area to slot exit surface area 0.8, chimney height and height of the outlet pipe 40 mm, tray clearance of the bubble-cap 10 mm, slot height 15 mm, the angle between obliquely angled slot and longitudinal edge of the hood=30 degrees, maximum length of the longitudinal edge of the hood 800 mm, reduction in the hood length in the peripheral region of the column down to 200 mm, distance between two hoods disposed on one line in the crossflow direction 66 mm, drain surface of the downcomer 1.5% based on the cross-sectional surface area of the tray, breadth between the two lower longitudinal edges of a hood 64 mm); 1.70 m above the uppermost Thormann tray there is a further, second collecting tray; 2300 mm above this collecting tray, 11 double-flow valve trays (height of the drainpipe 35 mm, orifice ratio 18%, the sum of the drain surface areas of the downcomers of two successive valve trays 10% of the column cross-sectional surface area) are in equidistant arrangement (tray separation=500 mm).

The separating column was operated as described in DE-A 10247240. The gas mixture for partial oxidation cooled to T=132° C. which was fed to it contained the following contents:
  26% by weight of acrylic acid,
  0.3% by weight of acetic acid,
  4.3% by weight of water,
  0.03% by weight of formic acid,
  0.07% by weight of formaldehyde,
  0.08% by weight of acrolein,
  0.02% by weight of propionic acid,
  0.4% by weight of furfurals,
  0.003% by weight of allyl acrylate,
  0.6% by weight of benzaldehyde,
  6.7% by weight of maleic anhydride,
  0.02% by weight of benzoic acid,
  0.09% by weight of acryloylpropionic acid,
  1.6% by weight of carbon dioxide,
  0.5% by weight of carbon monoxide,
  0.5% by weight of propane,
  0.2% by weight of propene,
  2.8% by weight of oxygen and
  55.7% by weight of nitrogen.

As described in DE-A 10247240, this gas mixture was separated in the separating column into 97.1% by weight acrylic acid (removal from the first collecting tray), an offgas stream comprising 0.1% by weight of acrylic acid (leaving at the top of the separating column), acid water comprising 5.5% by weight of acrylic acid (removal from the second collecting tray) and into a high boiler mixture comprising 22.8% by weight of acrylic acid.

The temperature at the top of the column was 36° C., the pressure at the top of the column 1.2 bar, the reflux ratio 4.3. The bottom temperature was 132° C. and the pressure directly above the surface of the bottoms was 1.56 bar.

Polymerization was inhibited in the liquid falling in the separating column as described in DE-A 10247240.

The 21 dual-flow trays above the removal point of the 97.1% by weight acrylic acid were operated as follows:
  gas loading: 2.1 $Pa^{0.5}$;
  liquid loading: 4.5 to 5.5 m/h;
  pressure drop: 1.6 to 1.7 mbar/tray;
  entrainment fraction: 10% by weight.

After a running time of 35 days, the sequence of 21 dual-flow trays had a total of about 50 kg of undesired polymer.

N.B.: Polymerization can also be inhibited as described in DE-A 10200583.

b) Example 1

The procedure of the comparative example was repeated, except that in the region of the 21 dual-flow trays, an identical portion of the passages was covered on each dual-flow tray while maintaining the gas loading.

This caused the pressure drop to rise to 2.4 to 2.5 mbar/tray.

The entrainment fraction per dual-flow tray rose to 25% by weight.

After a running time of 55 days, the region of the 21 dual-flow trays was still free of visible polymer formation.

The separating action was substantially unchanged compared to the comparative example.

N.B.: Polymerization can also be inhibited as described in DE-A 10200583.

c) Example 2

In a separating column whose separating internals were exclusively 30 uniform dual-flow trays in equidistant arrangement (diameter of the trays 2300 mm, tray separation 330 mm, uniform hole diameter 12 mm, orifice ratio 24%), a mixture comprising n-butyl acrylate and having the following contents was rectificatively separated:
  93.18% by weight of n-butyl acrylate,
  5.3% by weight of butyl butoxypropionate,
  1.3% by weight of butyl acryloylpropionate,
  0.02% by weight of butyl acetate,
  0.02% by weight of dibutyl ether,
  0.03% by weight of butyl propionate,
  0.02% by weight of propionic acid and
  0.13% by weight of phenothiazine.

The mixture was fed to the separating column below the lowermost tray. It was separated into a top product which contained 99.8% by weight of n-butyl acrylate and into a high boiler mixture which contained 27.9% by weight of n-butyl acrylate. The temperature at the top of the column was 81° C., the top pressure 110 mbar and the reflux ratio 0.4. The temperature in the bottoms of the column was 122° C. and the pressure at the surface of the bottom liquid was 185 mbar.

The gas loading was 2.1 $Pa^{0.5}$. The liquid loading was 2.1 m/h.

The pressure drop was 2.5 mbar/tray.

The entrainment fraction was 56% by weight.

After a running time of 155 days, the region of the dual-flow trays was free of visible polymer.

We claim:
1. A thermal separating process between at least one gaseous and at least one liquid stream, of which at least one comprises (meth)acrylic monomers, in a separating column containing separating internals, at least some of the separating internals being a sequence of sieve trays, wherein the improvement comprises:
  adjusting the streams so that at least some of the sieve trays are operated above an entrainment fraction of 10% by weight.

2. A thermal separating process as claimed in claim 1, wherein the separating internals contained in the separating column are exclusively mass transfer trays at least some of which being a sequence of sieve trays.

3. A thermal separating process as claimed in claim 1 or 2, wherein the separating internals contained in the separating column are, from bottom to top, dual-flow trickle sieve trays, hydraulically sealed crossflow trays and valve trays.

4. A thermal separating process as claimed in claim 1 or 2, wherein the separating internals contained in the separating column are exclusively trickle sieve trays.

5. A thermal separating process as claimed in claims 1 or 2, which is a process for fractional condensation, for rectification or for absorption.

6. A thermal separating process as claimed in claims 1 or 2, wherein at least some of the sieve trays are operated at an entrainment fraction of from 11 to 70% by weight.

7. A thermal separating process as claimed in claims 1 or 2, wherein at least some of the sieve trays are operated at an entrainment fraction of from 11 to 30% by weight.

8. A thermal separating process as claimed in claims 1 or 2, wherein all of the sieve trays are operated at an entrainment fraction of from 11 to 70% by weight.

9. A thermal separating process as claimed in claims 1 or 2, wherein all of the sieve trays are operated at an entrainment fraction of from 11 to 30% by weight.

10. A thermal separating process as claimed in claims 1 or 2, wherein the liquid stream comprises polymerization inhibitors.

11. A thermal separating process as claimed in claims 1 or 2, which is a process for fractionally condensing the product gas mixture of a catalytic gas phase oxidation of C3 precursor compounds to acrylic acid for preparing acrylic acid.

* * * * *